United States Patent
Appel et al.

(10) Patent No.: US 9,445,998 B2
(45) Date of Patent: Sep. 20, 2016

(54) PHARMACEUTICAL DOSAGE FORMS COMPRISING A LOW-SOLUBILITY DRUG AND A POLYMER

(71) Applicant: Bend Research, Inc., Bend, OR (US)

(72) Inventors: Leah E. Appel, Bend, OR (US); Walter C. Babcock, Bend, OR (US); Dwayne T. Friesen, Bend, OR (US); Roderick J. Ray, Bend, OR (US); Daniel T. Smithey, Bend, OR (US); Sheri L. Shamblin, North Stonington, CT (US); Ravi M. Shanker, Stonington, CT (US)

(73) Assignee: Bend Research, Inc., Bend, OR (US)

( * ) Notice: Subject to any disclaimer, the term of this patent is extended or adjusted under 35 U.S.C. 154(b) by 0 days.

(21) Appl. No.: 14/536,527

(22) Filed: Nov. 7, 2014

(65) Prior Publication Data
US 2015/0064264 A1    Mar. 5, 2015

Related U.S. Application Data

(63) Continuation of application No. 11/747,468, filed as application No. PCT/IB2005/002704 on Aug. 18, 2005, now abandoned.

(60) Provisional application No. 60/606,178, filed on Aug. 31, 2004.

(51) Int. Cl.
| | |
|---|---|
| *A61K 9/16* | (2006.01) |
| *A61K 31/496* | (2006.01) |
| *A61K 31/505* | (2006.01) |
| *A61K 9/00* | (2006.01) |
| *A61K 9/20* | (2006.01) |
| *A61K 9/28* | (2006.01) |

(52) U.S. Cl.
CPC ........... *A61K 9/1682* (2013.01); *A61K 9/1629* (2013.01); *A61K 9/1652* (2013.01); *A61K 31/496* (2013.01); *A61K 31/505* (2013.01); *A61K 9/0004* (2013.01); *A61K 9/205* (2013.01); *A61K 9/2846* (2013.01)

(58) Field of Classification Search
None
See application file for complete search history.

(56) References Cited

U.S. PATENT DOCUMENTS

| | | | |
|---|---|---|---|
| 5,277,916 A | 1/1994 | Dwyer et al. | |
| 6,150,366 A | 11/2000 | Arenson et al. | |
| 6,165,506 A | 12/2000 | Jain et al. | |
| 6,197,348 B1 | 3/2001 | Morella et al. | |
| 6,221,400 B1 | 4/2001 | Liversidge et al. | |
| 6,264,981 B1 | 7/2001 | Zhang et al. | |
| 2002/0006443 A1* | 1/2002 | Curatolo ................ | A61K 9/146 424/486 |
| 2002/0009494 A1 | 1/2002 | Curatolo et al. | |
| 2002/0012675 A1 | 1/2002 | Jain et al. | |
| 2002/0039594 A1 | 4/2002 | Unger | |
| 2003/0064108 A1 | 4/2003 | Lukas et al. | |
| 2003/0072801 A1 | 4/2003 | Curatolo | |
| 2003/0219489 A1* | 11/2003 | Curatolo ................ | A61K 9/146 424/488 |
| 2004/0076675 A1 | 4/2004 | Sugishita et al. | |
| 2005/0123616 A1* | 6/2005 | Appel .................. | A61K 9/1652 424/489 |
| 2005/0277651 A1* | 12/2005 | Zetina-Rocha ...... | C07D 417/12 514/254.04 |
| 2008/0286373 A1* | 11/2008 | Palepu ................. | A61K 9/1676 424/494 |
| 2009/0142404 A1 | 6/2009 | Appel et al. | |

FOREIGN PATENT DOCUMENTS

| | | |
|---|---|---|
| EP | 1027887 | 8/2000 |
| EP | 901786 | 6/2007 |
| EP | 1027885 | 7/2008 |
| WO | WO 9912549 | 3/1999 |
| WO | WO 0147495 | 7/2001 |
| WO | WO 0243704 | 6/2002 |
| WO | WO 03000226 | 1/2003 |
| WO | WO 03000238 | 1/2003 |
| WO | WO 03043606 | 5/2003 |
| WO | WO 03063833 | 8/2003 |
| WO | WO 2004014342 | 2/2004 |
| WO | WO 2005020929 | 3/2005 |
| WO | WO 2005065656 | 7/2005 |
| WO | WO 2005065660 | 7/2005 |

OTHER PUBLICATIONS

JA Westerhuis, "Multivariate Statistical Modelling of the Pharmaceutical Process of Wet Granulation and Tableting," PhD Thesis, University of Groningen, Sep. 22, 1997, Title page and pp. 13-38.

* cited by examiner

*Primary Examiner* — Robert A Wax
*Assistant Examiner* — Danah Al-Awadi
(74) *Attorney, Agent, or Firm* — Klarquist Sparkman, LLP

(57) ABSTRACT

A dosage form comprises a low-solubility drug, and a precipitation-inhibiting polymer. The drug is in a solubility-improved form and in the form of particles at least partially coated with the precipitation-inhibiting polymer.

7 Claims, 2 Drawing Sheets

PHARMACEUTICAL DOSAGE FORMS COMPRISING A LOW-SOLUBILITY DRUG AND A POLYMER

CROSS REFERENCE TO RELATED APPLICATIONS

This is a continuation of application Ser. No. 11/747,468, deposited on May 11, 2007 with a 35 U.S.C. §371(c) completion date of Feb. 6, 2009, which is the National Stage of International Application No. PCT/IB05/02704, filed Aug. 18, 2005, which claims priority to Provisional Application No. 60/606,178, filed Aug. 31, 2004, each of which is incorporated herein in its entirety by reference.

BACKGROUND

The present invention relates to pharmaceutical dosage forms comprising a low-solubility drug and a polymer.

It is known in the art that a low-solubility drug may be combined with a polymer to increase the concentration of dissolved drug in an aqueous use environment relative to a composition that does not contain the polymer. For example, Curatolo et al., U.S. Pat. No. 6,548,555 B1, disclose compositions comprising a basic drug admixed with a polymer selected from the group consisting of hydroxypropylmethyl cellulose acetate succinate (HPMCAS), cellulose acetate trimellitate (CAT), cellulose acetate phthalate (CAP), hydroxypropyl cellulose acetate phthalate (HPCAP), hydroxypropylmethyl cellulose acetate phthalate (HPMCAP), and methyl cellulose acetate phthalate (MCAP). The basic drug, when administered to a gastric use environment, initially dissolves to a high concentration. This high concentration is sustained by the presence of the polymer when the drug enters a higher pH intestinal use environment.

Curatolo, et al., US published patent application 2002/0006443A1, disclose mixtures of solubility-improved forms of drugs and a polymer. The solubility-improved form may be crystalline, such as a high-solubility salt or polymorph, that provides, at least temporarily, enhanced aqueous solubility relative to the lowest-energy crystalline drug form.

Curatolo, et al., US published patent application 2003/0072801 A1, disclose several solubilized drug forms combined with various polymers. The application discloses, among other things, such solubilized drug forms as nanoparticles and cyclodextrin complexes combined with polymers.

While not wishing to be bound by a particular theory, it is believed that the polymer, when combined with a solubilized drug, generally does not have the capacity to greatly solubilize insoluble drugs (that is, to increase the equilibrium solubility of free drug). Instead, it is believed the polymer primarily acts to slow the rate of precipitation or crystallization of the drug after the drug is initially dissolved. The presence of the polymer(s) thus allows the initially increased or enhanced concentration provided by the solubility-improved form of the drug to be at least partially maintained for at least a few minutes and, in some cases, for many hours. In addition, in cases where dissolution of the solubility-improved form of the drug is slow and precipitation of the low-solubility drug form, in the absence of the polymer, is fast, the presence of the polymer may result in the maximum concentration of drug observed being substantially higher than that observed in the absence of the polymer.

One possible mechanism for improving the dissolved drug concentration involves the association of the polymer and dissolved drug to form "polymer/drug assemblies." Such assemblies may constitute various forms, including polymeric micelles, high-energy polymer-drug aggregates ranging in size from a few nanometers to 1000 nanometers, polymer-stabilized drug colloids or polymer/drug complexes. An alternative view is that as dissolved drug begins to precipitate or crystallize from solution (e.g., as nucleation begins) the polymer adsorbs to these drug aggregates or nuclei, preventing, or at least retarding, the nucleation or crystal-growth process. In any case, the presence of the polymer serves to enhance the amount of drug that is dissolved or at least available for absorption. The various drug/polymer assemblies listed above are apparently quite labile and may contribute to the drug absorption process.

However, when the low-solubility drug and polymer are mixed together with other excipients to form a dosage form, the polymer and drug may become segregated or diluted relative to each other during manufacture of the dosage form. When the dosage form is then subsequently administered to an aqueous use environment, such as an in vitro dissolution test or the gastrointestinal tract of an animal, the drug and polymer may not be immediately adjacent to one another, which may impede the formation of polymer/drug assemblies. Alternatively, the dosage forms may provide variable performance due to segregation of the drug and polymer during manufacture. In addition, even when the polymer and drug remain uniformly mixed, during dissolution of the drug, the concentration of dissolved drug near the surface of the drug particles may exceed its equilibrium value and begin to precipitate or crystallize prior to encountering sufficient levels of dissolved polymer or polymer-colloids to inhibit such crystallization or inhibition.

Accordingly, it is desired to combine a low-solubility drug and precipitation-inhibiting polymer in a dosage form in a manner that facilitates reproducibly achieving concentration-enhancement of dissolved drug in a use environment, and/or provides or sustains higher concentrations of dissolved drug.

SUMMARY OF THE INVENTION

In one aspect, a dosage form comprises a low-solubility drug and a precipitation-inhibiting polymer. The low-solubility drug is in a solubility-improved form and in the form of particles at least partially coated with the precipitation-inhibiting polymer.

The dosage forms of the present invention ameliorate the problem of variability in performance by combining the drug and polymer together so that the drug and polymer remain in contact with each other during formation of the dosage form, and later during release of the drug from the dosage form. Since the polymer at least partially coats the drug, the drug and polymer remain in contact during formation of the dosage form. Even as the drug and polymer are combined with other excipients, such as binders, diluents, disintegrants, osmagents, or other such materials, nevertheless the drug and polymer are not diluted relative to each other during manufacture of the dosage form. Nor are the drug and polymer segregated from one another due to inhomogeneities that may occur when combining the drug and excipients that make up the dosage form. Thus, regardless of the amount of additional excipients or the degree of homogeneity of the materials used to form the dosage form, the polymer and drug remain in contact in the finished dosage form. As a consequence, the drug and polymer are still in contact as the drug is released from the dosage form into an aqueous use environment. This is advantageous to achieving good performance, since in the absence of the polymer the drug that begins to dissolve after release will soon begin to precipitate. However, when the drug and polymer are in contact with one another at the time of release into the aqueous use environment, the drug and polymer can begin to dissolve together in close proximity. This facilitates the formation of polymer/drug assemblies, or may allow the polymer to adsorb to drug aggregates or nuclei, preventing, or at least retarding, the nucleation or crystal-growth process. In any case, the close proximity of the polymer to the drug at the time of release into the use environment serves to enhance the amount of drug that remains dissolved or at least available for absorption.

In addition, at least partial coating of the drug particles by the polymer can retard the dissolution of the drug until the polymer is at least first partially dissolved. This is particularly important when the polymer is slow to dissolve relative to the drug or when the drug and polymer may be, at least temporarily in an environment where the polymer is relatively insoluble compared to the drug. For example, when the polymer is relatively insoluble at low pH, such as an enteric polymer, coating of the drug by the polymer may prevent or retard the dissolution of drug until it reaches an environment where the pH is high enough for the polymer to swell, disperse, or dissolve.

The foregoing and other objectives, features, and advantages of the invention will be more readily understood upon consideration of the following detailed description of the invention.

DETAILED DESCRIPTION OF THE INVENTION

The dosage forms of the present invention comprise a low-solubility drug and a precipitation-inhibiting polymer. The low-solubility drug is in the form of particles at least partially coated with the precipitation-inhibiting polymer. By "particles" is meant, when the drug is crystalline, individual crystals of the drug. When the drug is amorphous, "particles" refers to individual particles comprising drug in amorphous form. In general, the particles may range in size from about 0.1 µm to about 500 µm.

Figure 1:
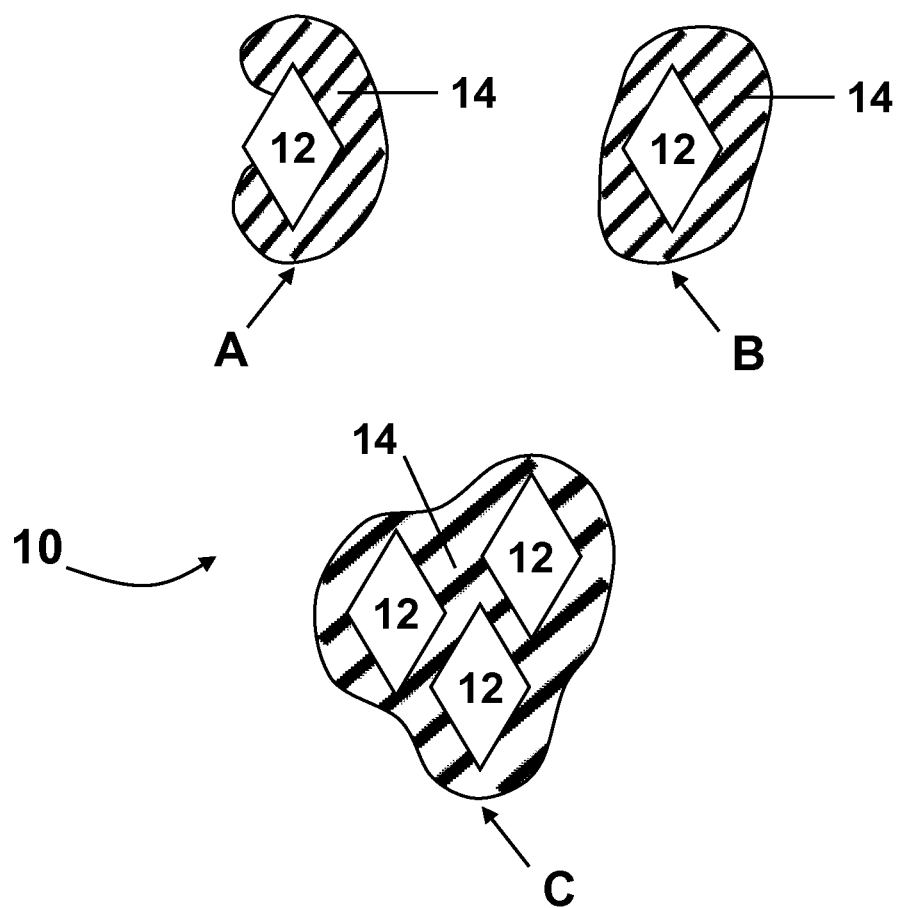
FIG. 1 shows schematically in cross section polymer coated drug particles.

By "at least partially coated" with a precipitation-inhibiting polymer means that the precipitation-inhibiting polymer partially coats at least a portion of the surface of the drug particles. The precipitation-inhibiting polymer may coat only a portion of the drug particle, or may fully coat or encapsulate the entire surface of the drug particle. For example, FIG. 1 shows schematically a composition 10 comprising particles 12 of crystalline drug with precipitation-inhibiting polymer coating 14. Coated particle A has a portion of the surface of the crystalline drug 12 coated with the precipitation-inhibiting polymer 14. Coated particle B has the crystalline drug 12 completely coated or encapsulated with the precipitation-inhibiting polymer 14. Thus, the compositions may contain particles that are partially coated with precipitation-inhibiting polymer, may contain particles that are completely coated, or may contain a mixture of partially and completely coated particles. The drug particles are coated such that at least a portion of the surface of the drug particle is in direct contact with the precipitation-inhibiting polymer. The at least partially coated particles are in contrast to a simple dry physical mixture of drug and polymer particles wherein both the drug and polymer are mixed in particulate form and wherein the particles of each are physically separate from one another.

Figure 2:
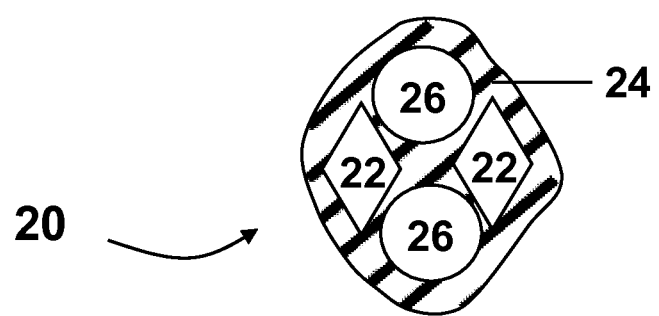
FIG. 2 shows schematically in cross section polymer coated particles comprising drug particles and polymer particles.

In another embodiment shown schematically in FIG. 2, a composition 20 comprises drug particles 22, precipitation-inhibiting polymer coating 24, and additional particles of precipitation-inhibiting polymer 26. The precipitation-inhibiting polymers 24 and 26 may be the same or different. In one preferred embodiment, the precipitation-inhibiting polymers 24 and 26 are both hydroxypropylmethyl cellulose acetate succinate. This embodiment has particular utility when it is desired to have a relatively high weight ratio of polymer to drug (e.g., a polymer to drug weight ratio of greater than about 0.5). The efficiency of the coating process used to coat the precipitation-inhibiting polymer onto the drug particles is a function of the amount of precipitation-inhibiting polymer that must be dissolved and coated onto the drug particles. In this embodiment, only a portion of the precipitation-inhibiting polymer is dissolved and coated, whereas the remainder is present as particles. Nonetheless, the resulting composition contains drug particles at least partially coated with the precipitation-inhibiting polymer, and also contain additional precipitation-inhibiting polymer 26, all of which are present in the composition 20.

The precipitation-inhibiting polymer coating and drug, while in contact with one another, are in separate phases. The drug particle, when a crystalline drug form, remains relatively pure drug, and retains its characteristic properties such as melting point or glass transition temperature. Thus, the polymer coated drug particles are in contrast to molecular dispersions or solid solutions of the drug in the polymer.

In addition, the drug particles may be either individually coated, or several drug particles may be coated with polymer and present in a single particle. For example, returning to FIG. 1, particle B is an individually coated drug crystal, while particle C consists of several drug crystals 12 coated with precipitation-inhibiting polymer 14. In cases where the drug particles are quite small, there can be many drug particles within the polymer-coated drug particle. For example, a polymer coated drug particle having a diameter of about 100 µm may contain more than one million drug particles that have a diameter on the order of 0.1 to 1 µm. Thus, the compositions may contain individually coated drug particles, may contain coated particles containing several drug particles, or both. In those embodiments in which the coated particles contain several drug particles, it is preferred that the coated particles remain small. It is preferred that the coated drug particles remain smaller than about 500 µm in average diameter. The particles may be smaller than about 100 µm, smaller than about 50 µm, or even smaller than about 20 µm in average diameter. Thus, the polymer coated drug particles are free flowing particulates that may be mixed and/or blended with other excipients to form a dosage form.

The dosage form may also contain one or more excipients in addition to the polymer coated drug particles. The invention finds particular utility where the dosage form contains an additional excipient. The polymer and drug remain in contact with one another and do not become segregated or diluted due to the presence of the excipient in the dosage form. The excipient may be combined with the polymer coated particles in any fashion. Thus, the drug and excipient may be coated together with the polymer. Alternatively, the excipient may be mixed or blended with the polymer coated particles subsequent to coating of the drug particles with polymer.

While the dosage form comprises polymer coated drug particles, the dosage form may also comprise drug that is not coated with a polymer. In addition, the dosage form may also comprise drug that is not in a solubility-improved form. For example, where the dosage form has an immediate release component and a sustained release component, the drug in the sustained release component may be in the solubility-improved form and may be at least partially coated with the polymer, while the drug in the immediate release component may be the lowest solubility form without any polymer coating.

The Drug

The term "drug" is conventional, denoting a compound having beneficial prophylactic and/or therapeutic properties when administered to an animal, especially humans. By "low-solubility drug" is meant that the drug may be either "substantially water-insoluble," which means that the drug has a minimum aqueous solubility at any physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. The invention finds greater utility as the solubility of the drug decreases. Thus, compositions of the present invention are preferred for low-solubility drugs having a minimum solubility of less than 10 mg/mL, more preferred for low-solubility drugs having a minimum solubility of less than 1 mg/mL, more preferred for low-solubility drugs having a minimum solubility of less than 0.5 mg/mL, and even more preferred for low-solubility drugs having a minimum solubility of less than 0.1 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

Each named drug should be understood to include any pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, neutral forms, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxyl)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethylphenoxy)-pyridin-4-yl]-(1-ethylpropyl)-amine, 3,5-dimethyl-4-(3'-pentoxy)-2-(2',4',6'-trimethylphenoxyl)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesteryl ester transfer protein (CETP) inhibitors include[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R, 4S]4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester, (2R)-3-[[3-(4-chloro-3-ethylphenoxy)phenyl][[3-(1,1,2,2-tetrafluoroethoxyl)phenyl]methyl]amino]-1,1,1-trifluoro-2-propanol, the drugs disclosed in commonly owned U.S. patent application Ser. Nos. 09/918,127 and 10/066,091, both of which are incorporated herein by reference in their entireties for all purposes, and the drugs disclosed in the following patents and published applications: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

The low-solubility drug is in a solubility-improved form. The term "solubility-improved form" refers to a form of the drug alone that, when delivered to an in vivo use environment (such as, for example, the gastrointestinal tract of a mammal) or an in vitro use environment (such as distilled water, phosphate buffered saline or a Model Fasted Duodenal solution described below) provides, at least temporarily, a maximum concentration of drug that is at least 1.25-fold the equilibrium concentration provided by the lowest solubility form of the drug known, a faster dissolution rate of the drug, or both. For example, for a basic drug, if the free base form of the drug provides an equilibrium dissolved drug concentration of 10 micrograms/ml in an in vitro test solution, the solubility-improved form of the drug would provide a maximum dissolved drug concentration of at least 12.5 micrograms/ml. Examples of "solubility-improved forms" include but are not limited to: (1) a crystalline highly soluble form of the drug such as a salt; (2) a high-energy crystalline form of the drug; (3) a hydrate or solvate crystalline form of a drug; (4) an amorphous form of a drug (for a drug that may exist as either amorphous or crystalline); (5) drug particles having reduced or small particle size; (6) drug in semi-ordered from in which the drug may have properties that lie between those of a crystalline form of the drug and an amorphous form of the drug; and (7) drug in a cyclodextrin complex. the solubility improved form may comprise a mixture of two or more of such solubility-improved forms.

In one aspect of the invention, the solubility-improved form of the drug is crystalline and is a highly soluble salt form of the drug. As used herein, "highly soluble salt form" means that the drug is in a salt form that provides solubility improvement as described below. The drug can be any pharmaceutically acceptable salt form of a basic, acidic, or zwitterionic drug that meets this criteria. Examples of salt forms for basic drugs include the chloride, bromide, acetate, iodide, mesylate, phosphate, maleate, citrate, sulfate, tartrate, lactate salts and the like. Examples of salt forms for acidic drugs include the sodium, calcium, potassium, zinc, magnesium, lithium, aluminum, meglumine, diethanolamine, benzathine, choline, and procaine salts and the like. These salts can also be used for zwitterionic drugs.

An example of a drug having a crystalline highly soluble salt form is ziprasidone. Ziprasidone hydrochloride monohydrate has a solubility of about 10 μgA/mL (expressed as the free base) in water, whereas the free base form has a solubility of less than about 0.2 μgA/mL under the same conditions. Thus, crystalline ziprasidone hydrochloride is a solubility-improved form relative to the crystalline free base form of ziprasidone. When dosed to a buffered aqueous solution such as phosphate buffered saline at pH 6.5, the crystalline ziprasidone hydrochloride monohydrate dissolves such that it achieves a maximum concentration of about 0.4 to 1.2 μgA/m L. However, at equilibrium, the drug crystallizes from such solutions as the free base form such that the equilibrium solubility of ziprasidone is about 0.2 μgA/mL.

Alternatively, in another separate aspect of the invention, the drug exists in a high-energy crystalline form that has improved solubility relative to a low-energy crystalline form. It is known that some drugs may crystallize into one of several different crystal forms. Such crystal forms are often referred to as "polymorphs." As used herein, "a high-energy crystalline form" means that the drug is in a crystal form which provides solubility improvement as described below. An example of such a drug is the "A1" form of 5-chloro-1H-indole-2-carboxylic acid [(1S)-benzyl-3-((3R,4S)-dihydroxypyrrolidin-1-yl)-(2R)-hydroxy-3-oxpropyl]amide, which has a solubility in phosphate buffered saline (PBS at pH 6.5) of about 480 μg/mL while the "A2" form has a solubility in PBS of only 87 μg/m L.

In yet another separate aspect of the invention, although the drug may be capable of existing in either the amorphous or crystalline form, in the composition it is in the amorphous form. Preferably, at least a major portion of the drug is amorphous. By "amorphous" is meant simply that the drug is in a non-crystalline state. As used herein, the term "a major portion" of means that at least 60 wt % of the drug in the composition is in the amorphous form, rather than the crystalline form. Preferably, the drug is substantially amorphous. As used herein, "substantially amorphous" means that the amount of drug in crystalline form does not exceed about 25 wt %. More preferably, the drug is "almost completely amorphous," meaning that the amount of drug in the crystalline form does not exceed about 10 wt %. Amounts of crystalline drug may be measured by Powder X-Ray Diffraction (PXRD), Scanning Electron Microscope (SEM) analysis, differential scanning calorimetry (DSC), or any other standard quantitative measurement. The drug in its amorphous form provides in at least an in vitro test medium a maximum concentration of the drug that is greater than the maximum concentration of the drug provided by the drug in crystalline form. An example of such a drug is 5-chloro-1H-indole-2-carboxylic acid [(1S)-benzyl-3-((3R,4S)-dihydroxypyrrolidin-1-yl-)-(2R)-hydroxy-3-oxypropyl]amide, the maximum dissolved drug concentration provided by the amorphous form of which is about 600 μg/mL, while the maximum dissolved drug concentration provided by the "A2" crystalline form is only 87 μg/mL, both as measured in pH 6.5 PBS solution.

The amorphous form of the drug may be any form in which the drug is amorphous. Examples of amorphous forms of drug include solid amorphous dispersions of drug in a polymer, such as disclosed in commonly assigned US published patent application 2002/0009494A1 herein incorporated by reference. Alternatively, the drug may be adsorbed in amorphous form on a solid substrate, such as disclosed in commonly assigned US published patent application 2003/0054037A1, herein incorporated by reference. As yet another alternative, amorphous drug may be stabilized using a matrix material, such as disclosed in commonly assigned US Patent application 2003/0104063A1, herein incorporated by reference.

Another solubility-improved form of drug is drug in a semi-ordered state, such as disclosed in commonly assigned U.S. Provisional Patent Application Ser. No. 60/403,087 filed Aug. 12, 2002, herein incorporated by reference.

In yet another embodiment, the solubility-improved form comprises small drug particles that improve the dissolution rate of the drug relative to the bulk crystalline form of the drug. By small particle size is meant that the drug particles have a mean diameter of less than 50 microns, more preferably less than 20 microns, and even more preferably less than 10 microns. A particularly preferred and simple method for forming small particles of drug involves breaking larger diameter particles into smaller diameter particles. Particle size reduction may be accomplished by any conventional method, such as by milling, or grinding. Exemplary milling devices include a chaser mill, ball mill, vibrating ball mill, hammer mill, impact grinding mill, fluid energy mill (jet mill), and centrifugal-impact pulverizers. Alternatively, small particles may be formed by atomization or precipitation. A preferred method for reducing the drug particle size is jet milling. Small drug particles can also be formed by other means, such as dissolution in a solvent such as alcohol or water followed by precipitation by mixing with a nonsolvent. Another method to reduce particle size is by melting or dissolving the drug in a solvent and atomizing the resulting liquid by spray congealing or spray drying to form a powder. The size of the drug particles needed to enhance drug dissolution compared with the bulk crystalline form of the drug will depend on the particular drug. In general, however, dissolution rate tends to increase as the drug particle size decreases. The average particle size may be less than 100 microns, less than 50 microns, or even less than 10 microns. For example, in the case of the drug ziprasidone, jet-milled ziprasidone may have a mean particle size of less than about 10 microns, and more preferably less than about 5 microns. As described above, when a solubility improved form of the a drug, such as a salt, is dosed to a buffered solution, such as phosphate buffered saline, with a pH of about 6 to 7.5, a lower solubility form of the drug may ultimately precipitate from solution. In such cases, the maximum dissolved concentration achieved is determined by the relative values of dissolution of the solubility improved drug form and the precipitation or crystallization rate of the lower solubility form. Thus, increasing the rate of dissolution of the drug by reduction of particle size can yield at least temporarily a higher maximum drug concentration than that achieved by dissolution of larger drug particles.

Another solubility-improved form of a drug comprises drug combined with a cyclodextrin as an inclusion complex. As used herein, the term "cyclodextrin" refers to all forms and derivatives of cyclodextrin. Particular examples of cyclodextrin include a-cyclodextrin, b-cyclodextrin, and g-cyclodextrin. Exemplary derivatives of cyclodextrin include mono- or polyalkylated b-cyclodextrin, mono- or polyhydroxyalkylated b-cyclodextrin, such as hydroxypropyl b-cyclodextrin (hydroxypropylcyclodextrin), mono, tetra or hepta-substituted b-cyclodextrin, and sulfoalkyl ether cyclodextrins (SAE-CD), such as sulfobutylether cyclodextrin (SBECD). The drug and cyclodextrin are complexed together. For example, the active drug and sulfoalkyl ether cyclodextrin (SAE-CD) may be preformed into a complex prior to the preparation of the final formulation. The complex may be formed by lyophilizing both the drug and cyclodextrin together to form a co-lyophile.

Several methods, such as an in vitro dissolution test or a membrane permeation test may be used to determine if a form of the drug is a solubility-improved form and the degree of solubility improvement. An in vitro dissolution test may be performed by adding the solubility-improved form of drug to a dissolution test media, such as model fasted duodenal (MFD) solution, phosphate buffered saline (PBS) solution, or distilled water and agitating to promote dissolution. An appropriate PBS solution is an aqueous solution comprising 20 mM $Na_2HPO_4$, 47 mM $KH_2PO_4$, 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-palmitoyl-2-oleyl-sn-glycero-3-phosphocholine. Water is a preferred dissolution media for some fast precipitating salts. In cases where the solubility-improved form is an ionic salt of the drug it is often observed that when neutral buffer solutions (pH 6 to 8) are used, the solubility-improved form rapidly converts to the lowest energy form of the drug, typically the neutral crystalline form. In such cases it may be preferred to use an unbuffered test medium such as distilled water as the dissolution medium.

In one method for evaluating whether the form is a solubility-improved form, the solubility-improved form of the drug when tested in an in vitro dissolution test meets at least one, and preferably both, of the following conditions. The first condition is that the solubility-improved form provides a higher maximum dissolved drug concentration (MDC) of drug in the in vitro dissolution test relative to a control composition consisting of the lowest solubility crystalline form of the drug. That is, once the solubility-improved form is introduced into a use environment, the solubility-improved form provides a higher aqueous concentration of dissolved drug relative to the control composition. The control composition is the lowest solubility, bulk crystalline form of the drug alone. Preferably, the solubility-improved form provides an MDC of drug in aqueous solution that is at least 1.25-fold that of the control composition, more preferably at least 2-fold, and most preferably at least 3-fold. For example, if the MDC provided by the test composition is 22 µg/ml, and the MDC provided by the control composition is 2 µg/ml, the solubility-improved form provides an MDC that is 11-fold that provided by the control composition.

The second condition is that the solubility-improved form provides a higher dissolution area under the concentration versus time curve (AUC) of dissolved drug in the in vitro dissolution test relative to a control composition consisting of an equivalent amount of drug alone. More specifically, in the in vitro use environment, the solubility-improved form provides an AUC for any 90-minute period from about 0 to about 270 minutes following introduction to the use environment that is at least 1.25-fold that of the control composition described above. Preferably, the AUC provided by the composition is at least 2-fold, more preferably at least 3-fold that of the control composition.

An in vitro test to evaluate enhanced drug concentration in aqueous solution can be conducted by (1) adding with agitation a sufficient quantity of control composition, that is, the lowest solubility crystalline drug alone, to the in vitro test medium, such as distilled water or an MFD or a PBS solution, to achieve equilibrium concentration of drug; (2) in a separate test, adding with agitation a sufficient quantity of test composition (e.g., the solubility-improved form) in the same test medium, such that if all drug dissolved, the theoretical concentration of drug would exceed the equilibrium concentration provided by the control composition by a factor of at least 2, and preferably by a factor of at least 10; and (3) comparing the measured MDC and/or aqueous AUC of the test composition in the test medium with the equilibrium concentration, and/or with the aqueous AUC of the control composition. In conducting such a dissolution test, the amount of test composition or control composition used is an amount such that if all of the drug dissolved, the drug concentration would be at least 2-fold, preferably at least 10-fold, and most preferably at least 100-fold that of the equilibrium concentration.

The concentration of dissolved drug is typically measured as a function of time by sampling the test medium and plotting drug concentration in the test medium vs. time so that the MDC can be ascertained. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, (in less than about 30 minutes), the time interval used to calculate AUC is from time equals zero to time equals 90 minutes. However, if the AUC of a composition over any 90-minute time period described above meets the criterion of this invention, then the drug is considered to be in a solubility-improved form.

To avoid large drug particulates that would give an erroneous determination, the test solution is either filtered or centrifuged. "Dissolved drug" is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred solubility-improved forms. It should be recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

In another method for evaluation of whether a drug form is a solubility-improved form, the dissolution rate of the solubility improved form is measured and compared to the dissolution rate of the bulk crystalline form of the lowest solubility form of the drug. The dissolution rate may be tested in any appropriate dissolution media, such as PBS solution, MFD solution, or distilled water. Distilled water is a preferred dissolution media for salt forms that rapidly precipitate. The dissolution rate of the solubility-improved form is greater than the dissolution rate of the lowest solubility form of the drug in its bulk crystalline form. Preferably, the dissolution rate is 1.25-fold that of the lowest solubility form of the drug, more preferably at least 2-fold, and even more preferably at least 3-fold that of the lowest solubility form of the drug.

Alternatively, an in vitro membrane-permeation test may be used to determine if the drug is in a solubility-improved form. In this test, the solubility-improved form is placed in, dissolved in, suspended in, or otherwise delivered to the aqueous solution to form a feed solution. The aqueous solution can be any physiologically relevant solution, such as an MFD or PBS solution, as described above. After forming the feed solution, the solution may be agitated to dissolve or disperse the solubility-improved form therein or may be added immediately to a feed solution reservoir. Alternatively, the feed solution may be prepared directly in a feed solution reservoir. Preferably, the feed solution is not filtered or centrifuged after administration of the solubility-improved form prior to performing the membrane-permeation test.

The feed solution is then placed in contact with the feed side of a microporous membrane, the feed side surface of the microporous membrane being hydrophilic. The portion of the pores of the membrane that are not hydrophilic are filled with an organic fluid, such as a mixture of decanol and decane, and the permeate side of the membrane is in fluid communication with a permeate solution comprising the organic fluid. Both the feed solution and the organic fluid remain in contact with the microporous membrane for the duration of the test. The length of the test may range from several minutes to several hours or even days.

The rate of transport of drug from the feed solution to the permeate solution is determined by measuring the concentration of drug in the organic fluid in the permeate solution as a function of time or by measuring the concentration of drug in the feed solution as a function of time, or both. This can be accomplished by methods well known in the art, including by use of ultraviolet/visible (UV/Vis) spectroscopic analysis, high-performance liquid chromatography (HPLC), gas chromatography (GC), nuclear magnetic resonance (NMR), infra red (IR) spectroscopic analysis, polarized light, density, and refractive index. The concentration of drug in the organic fluid can be determined by sampling the organic fluid at discrete time points and analyzing for drug concentration or by continuously analyzing the concentration of drug in the organic fluid. For continuous analysis, UV/Vis probes may be used, as can flow-through cells. In all cases, the concentration of drug in the organic fluid is determined by comparing the results against a set of standards, as well known in the art.

From these data, the maximum flux of drug across the membrane is calculated by multiplying the maximum slope of the concentration of drug in the permeate solution versus time plot by the permeate volume and dividing by the membrane area. This maximum slope is typically determined during the first 10 to 90 minutes of the test, where the concentration of drug in the permeate solution often increases at a nearly constant rate following a short time lag of a few minutes. At longer times, as more of the drug is removed from the feed solution, the slope of the concentration versus time plot decreases. Often, the slope approaches zero as the driving force for transport of drug across the membrane approaches zero; that is, the drug in the two phases approaches equilibrium. The maximum flux is determined either from the linear portion of the concentration versus time plot, or is estimated from a tangent to the concentration versus time plot at time where the slope is at its highest value if the curve is non-linear. Further details of this membrane-permeation test are presented in co-pending U.S. Patent Application Ser. No. 60/557,897, entitled "Method and Device for Evaluation of Pharmaceutical Compositions," filed Mar. 30, 2004, incorporated herein by reference.

A typical in vitro membrane-permeation test to evaluate solubility-improved drug forms can be conducted by (1) administering a sufficient quantity of test composition (that is, the solubility-improved form of the drug) to a feed solution, such that if all of the drug dissolved, the theoretical concentration of drug would exceed the equilibrium concentration of the drug by a factor of at least 2; (2) in a separate test, adding an equivalent amount of control composition (that is, the lowest solubility form of the drug) to an equivalent amount of test medium; and (3) determining whether the measured maximum flux of drug provided by the test composition is at least 1.25-fold that provided by the control composition. A composition is a solubility-improved form if, when dosed to an aqueous use environment, it provides a maximum flux of drug in the above test that is at least about 1.25-fold the maximum flux provided by the control composition. Preferably, the maximum flux provided by the compositions are at least about 1.5-fold, more preferably at least about 2-fold, and even more preferably at least about 3-fold that provided by the control composition.

Precipitation-Inhibiting Polymers

Precipitation-inhibiting polymers suitable for use with the present invention should be inert, in the sense that they do not chemically react with drug in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Precipitation-inhibiting polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

A preferred class of precipitation-inhibiting polymers comprises polymers that are "amphiphilic" in nature, meaning that the polymer has hydrophobic and hydrophilic portions. The hydrophobic portion may comprise groups such as aliphatic or aromatic hydrocarbon groups. The hydrophilic portion may comprise either ionizable or non-ionizable groups that are capable of hydrogen bonding such as hydroxyls, carboxylic acids, esters, amines or amides.

One class of precipitation-inhibiting polymers suitable for use with the present invention comprises neutral non-cellulosic polymers. Exemplary polymers include: vinyl polymers and copolymers having substituents of hydroxyl, alkylacyloxy, or cyclicamido; polyvinyl alcohols that have at least a portion of their repeat units in the unhydrolyzed (vinyl acetate) form; polyvinyl alcohol polyvinyl acetate copolymers; polyvinyl pyrrolidone; polyoxyethylene-polyoxypropylene copolymers, also known as poloxamers; and polyethylene polyvinyl alcohol copolymers.

Another class of precipitation-inhibiting polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; proteins; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers, and polyoxyethylene-polyoxypropylene copolymers. Exemplary commercial grades of such copolymers include the EUDRAGITS, which are copolymers of methacrylates and acrylates, and the PLURONICS or LUTROLS supplied by BASF, which are polyoxyethylene-polyoxypropylene copolymers.

A preferred class of precipitation-inhibiting polymers comprises ionizable and neutral cellulosic polymers with at least one ester- and/or ether-linked substituent in which the polymer has a degree of substitution of at least 0.1 for each substituent.

It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.1 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at at least a portion of the hydroxyl groups present on the saccharide repeat units of the polymer with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl methyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer. Neutral polymers suitable for use in the present invention are more fully disclosed in commonly assigned pending U.S. patent application Ser. No. 10/175,132, filed Jun. 18, 2002, herein incorporated by reference.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic group may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethyl ethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxypropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate, and carboxymethyl ethyl cellulose.

While, as listed above, a wide range of polymers may be used, the inventors have found that relatively hydrophobic polymers have shown the best performance as demonstrated in vitro dissolution tests. In particular, cellulosic polymers that are aqueous insoluble in their nonionized state but are aqueous soluble in their ionized state perform particularly well. A particular subclass of such polymers are the so-called "enteric" polymers, which include, for example, hydroxypropyl methyl cellulose acetate succinate (HPMCAS), hydroxypropyl methyl cellulose phthalate (HPMCP), cellulose acetate phthalate (CAP), cellulose acetate trimellitate (CAT), and carboxymethyl ethyl cellulose (CMEC). In addition, non-enteric grades of such polymers, as well as closely related cellulosic polymers, are expected to perform well due to the similarities in physical properties.

Thus, especially preferred polymers are hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl methyl cellulose acetate phthalate, cellulose acetate terephthalate, cellulose acetate isophthalate, and carboxymethyl ethyl cellulose (CMEC). The most preferred ionizable cellulosic polymers are hydroxypropyl methyl cellulose acetate succinate, hydroxypropyl methyl cellulose phthalate, cellulose acetate phthalate, cellulose acetate trimellitate, and carboxymethyl ethyl cellulose.

While specific polymers have been discussed as being suitable for use in the dosage forms of the present invention, blends of such polymers may also be suitable. Thus the term "polymer" is intended to include blends of polymers in addition to a single species of polymer.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer that has a pKa of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned copending U.S. patent application Ser. No. 10/175,566 entitled "Pharmaceutical Compositions of Drugs and Neutralized Acidic Polymers" filed Jun. 17, 2002, the relevant disclosure of which is incorporated by reference.

In addition, the preferred polymers listed above, that is amphiphilic cellulosic polymers, tend to have greater precipitation-inhibiting properties relative to the other polymers of the present invention. Generally those precipitation-inhibiting polymers that have ionizable substituents tend to perform best. In vitro tests of compositions with such polymers tend to have higher MDC and AUC values than compositions with other polymers of the invention.

The particles of low-solubility drug are at least partially coated with a sufficient amount of precipitation-inhibiting polymer to improve the concentration of dissolved drug relative to uncoated particles of the low-solubility drug alone (that is, particles of drug in solubility-improved form but no precipitation-inhibiting polymer). Several methods, such as an in vitro dissolution test or a membrane permeation test may be used to evaluate precipitation-inhibiting polymers and the degree of concentration enhancement provided by the polymers. It has been determined that enhanced drug concentration in in vitro dissolution tests or in membrane permeation tests in MFD solution or in PBS solution are good indicators of in vivo performance and bioavailability. When tested using an in vitro dissolution test, described above, the compositions meet at least one, and preferably both, of the following conditions. The first condition is that the composition increases the maximum dissolved drug concentration (MDC) of drug in the in vitro dissolution test relative to a control composition consisting of an equivalent amount of drug but no polymer. That is, once the composition is introduced into an environment of use, the composition provides an increased aqueous MDC of drug relative to the control composition. The control composition consists of the solubility-improved form of drug alone (without the precipitation-inhibiting polymer). Preferably, the inventive compositions provide an MDC of drug in aqueous solution that is at least 1.25-fold that of the control composition, more preferably at least 2-fold, and most preferably at least 3-fold. For example, if the MDC provided by the test composition is 5 mg/ml, and the MDC provided by the control composition is 1 mg/ml, the test composition provides an MDC that is 5 fold that provided by the control composition.

The second condition is that the polymer coated drug particle composition provides an increased dissolution area under the concentration versus time curve (AUC) of drug in the in vitro dissolution test relative to a control composition consisting of an equivalent amount of the drug in solubility-improved form but no polymer. (The calculation of an AUC is a well-known procedure in the pharmaceutical arts and is described, for example, in Welling, "Pharmacokinetics Processes and Mathematics," ACS Monograph 185 (1986).) More specifically, in the environment of use, the composition of low-solubility drug and polymer provides an AUC for any 90-minute period of from about 0 to about 270 minutes following introduction to the use environment that is at least 1.25-fold that of the control composition described above. Preferably, the AUC provided by the composition is at least 2-fold, more preferably at least 3-fold that of the control composition.

A typical in vitro test to evaluate enhanced drug concentration in aqueous solution can be conducted by (1) adding with agitation a sufficient quantity of control composition, that is, the solubility-improved form of the drug alone, to the in vitro test medium, such as an MFD or a PBS solution, to achieve equilibrium concentration of drug; (2) in a separate test, adding with agitation a sufficient quantity of test composition (e.g., the composition comprising polymer coated drug particles) in the same test medium, such that if all drug dissolved, the theoretical concentration of drug would exceed the equilibrium concentration of drug by a factor of at least 2, and preferably by a factor of at least 10; and (3) comparing the measured MDC and/or aqueous AUC of the test composition in the test medium with the equilibrium concentration, and/or with the aqueous AUC of the control composition. In conducting such a dissolution test, the amount of test composition or control composition used is an amount such that if all of the drug dissolved, the drug concentration would be at least 2-fold, preferably at least 10-fold, and most preferably at least 100-fold that of the equilibrium concentration.

Alternatively, an in vitro membrane-permeation test may be used to determine if the polymer coated drug particle composition provides concentration enhancement relative to the control composition. In this test, described above, the composition is placed in, dissolved in, suspended in, or otherwise delivered to the aqueous solution to form a feed solution. A typical in vitro membrane-permeation test to evaluate polymer coated drug particles can be conducted by (1) administering a sufficient quantity of test composition (that is, the solubility-improved drug form coated with precipitation-inhibiting polymer) to a feed solution, such that if all of the drug dissolved, the theoretical concentration of drug would exceed the equilibrium concentration of the drug by a factor of at least 2; (2) in a separate test, adding an equivalent amount of control composition (that is, the solubility-improved form of the drug alone) to an equivalent amount of test medium; and (3) determining whether the measured maximum flux of drug provided by the test composition is at least 1.25-fold that provided by the control composition. The solubility-improved form and precipitation-inhibiting polymer, when dosed to an aqueous use environment, provide a maximum flux of drug in the above test that is at least about 1.25-fold the maximum flux provided by the control composition. Preferably, the maximum flux provided by the test composition is at least about 1.5-fold, more preferably at least about 2-fold, and even more preferably at least about 3-fold that provided by the control composition.

Alternatively, dosage forms containing the polymer coated solubility-improved drug form particles, when dosed orally to a human or other animal in the fasted state, provide an AUC in drug concentration in the blood that is at least about 1.25-fold, preferably at least about 2-fold, preferably at least about 3-fold, preferably at least about 5-fold, and even more preferably at least about 10-fold that observed when a control dosage form is dosed. By drug concentration in the blood is meant the concentration of drug in blood, in serum, or in plasma. The control dosage form is identical to the test dosage form, except with no precipitation-inhibiting polymer. It is noted that such dosage forms can also be said to have a relative bioavailability of from about 1.25-fold to about 10-fold that of the control dosage form.

Alternatively, the dosage forms, when dosed orally to a human or other animal, provide a maximum concentration of drug in the blood ($C_{max}$) that is at least 1.25-fold that observed when a control dosage form is dosed. Preferably, the blood $C_{max}$ is at least about 2-fold, and more preferably at least about 3-fold that of the control composition.

Relative bioavailability and $C_{max}$ provided by the dosage forms can be tested in vivo in animals or humans using conventional methods for making such a determination. An in vivo test, such as a crossover study, may be used to determine whether a dosage form provides an enhanced relative bioavailability or $C_{max}$ compared with a control dosage form as described above. In an in vivo crossover study a test dosage form of the present invention comprising polymer coated solubility-improved drug form particles is dosed to half a group of test subjects and, after an appropriate washout period (e.g., one week) the same subjects are dosed with a control dosage form that is identical except with no polymer. The other half of the group is dosed with the control dosage form first, followed by the test dosage form. The relative bioavailability is measured as the concentration in the blood versus time area under the curve (AUC) determined for the test group divided by the AUC in the blood provided by the control composition. Preferably, this test/control ratio is determined for each subject, and then the ratios are averaged over all subjects in the study. In vivo determinations of AUC and $C_{max}$ can be made by plotting the blood concentration of drug along the ordinate (y-axis) against time along the abscissa (x-axis).

Process for Coating Drug Particles

The drug particles may be at least partially coated with the precipitation-inhibiting polymer using any conventional method. The precipitation-inhibiting polymer must be coated onto the drug particles so that the precipitation-inhibiting polymer forms a film or coating directly on the surface of the drug particle. In general, the coating process coats the precipitation-inhibiting polymer directly onto at least a portion of the surface of the drug particles. This allows the drug and precipitation-inhibiting polymer to be in direct contact with one another, and not to be diluted relative to each other by other excipients. The coating process also coats the drug particles without creating large (e.g., >500 μm) aggregates of drug and polymer. The resulting polymer coated drug particles should have a mean diameter of less than about 500 μm, and should be free flowing so as to facilitate blending of the polymer coated particles with other excipients.

A preferred method to coat the drug particles with precipitation-inhibiting polymer is to spray dry the drug and precipitation-inhibiting polymer together. The term "spray drying" is used conventionally and broadly refers to processes involving breaking up liquid mixtures or suspensions into small droplets (atomization) and rapidly removing solvent from the droplets in a container where there is a strong driving force for evaporation of solvent. This method has particular utility when the drug particles are small (such as less than 200 microns).

To at least partially coat the drug particles with precipitation-inhibiting polymer by spray drying, first a suspension of drug particles and dissolved precipitation-inhibiting polymer is formed in a solvent. The solvent is chosen based on the following characteristics: (1) the drug is insoluble or only slightly soluble in the solvent; (2) the polymer is soluble in the solvent; and (3) the solvent is relatively volatile. Preferably, the solubility of the drug in the solvent is less than 5 wt % of the amount of drug suspended in the spray solution, more preferably less than 1 wt % of the amount of drug suspended in the spray solution, and even more preferably less than 0.5 wt % of the amount of drug suspended in the spray solution. For example, if the spray solution contains 10 wt % drug, the drug preferably has a solubility of less than 0.5 wt %, more preferably less than 0.1 wt %, and even more preferably less than 0.05 wt % in the solvent. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, THF, cyclic ethers, and 1,1,1-trichloroethane. Mixtures of solvents, such as 50% methanol and 50% acetone, may also be used, as can mixtures with water as long as the polymer is sufficiently soluble to make the spray-drying process practicable and as long as the drug is sufficiently insoluble to remain in suspension and not dissolved. In some cases it may be desired to add a small amount of water to aid solubility of the polymer in the spray solution.

The relative amounts of drug suspended in the solvent and precipitation-inhibiting polymer dissolved in the solvent are chosen to yield the desired drug to precipitation-inhibiting polymer ratio in the resulting particles. For example, if a composition having a drug to precipitation-inhibiting polymer weight ratio of 0.33 (25 wt % drug) is desired, then the spray solution comprises 1 part drug and 3 parts precipitation-inhibiting polymer in the solvent. The total solids content of the spray solution is preferably sufficiently high so that the spray solution results in efficient production of the coated particles. The total solids content refers to the amount of solid drug, dissolved precipitation-inhibiting polymer and other excipients dissolved in the solvent. For example, to form a spray solution having a 5 wt % dissolved solids content and which results in a particle having a 25 wt % drug loading, the spray solution would comprise 1.25 wt % drug, 3.75 wt % precipitation-inhibiting polymer and 95 wt % solvent. To achieve good yield, the spray solution preferably has a solids content of at least 3 wt %, more preferably at least 5 wt %, and even more preferably at least 10 wt %. Given the wide range of precipitation-inhibiting polymer molecular weights that may be chosen, the best solids content can vary widely from less than 1 wt % to more than 30 wt %. However, the solids content should not be too high, or else the spray solution may be too viscous to atomize efficiently into small droplets.

Spray drying to form polymer coatings around drug particles is well known and is described in, for example, U.S. Pat. No. 4,767,789, U.S. Pat. No. 5,013,537, and U.S. published patent application 2002/0064108A1, herein incorporated by reference.

Alternatively, the polymer may be coated around the drug crystals using a rotary disk atomizer, as described in U.S. Pat. No. 4,675,140, herein incorporated by reference.

Alternatively, the precipitation-inhibiting polymer may be sprayed onto the drug particles in a high shear mixer or a fluid bed.

The amount of polymer coated onto the solubility-improved drug form is sufficient to provide concentration-enhancement of the drug relative to a control composition consisting of the drug alone as described above. Depending on the nature of the precipitation-inhibiting polymer and drug, the ratio of polymer to drug may vary from about 0.01 to about 100. Good results are generally achieved where the polymer to drug weight ratio is at least about 0.11 (at least about 10 wt % polymer), more preferably at least about 0.33 (at least about 25 wt % polymer), even more preferably at least about 0.66 (at least about 40 wt % polymer), and even more preferably at least about 1 (at least about 50 wt % polymer). In a preferred embodiment, the polymer to drug weight ratio ranges from about 1 to about 4 (e.g., 50 wt % polymer to 80 wt % polymer). However, since it is often desired to limit the size of the dosage form, the amount of precipitation-inhibiting polymer may be less than the amount that provides the greatest degree of concentration enhancement. When calculating the weight ratio of polymer to drug, the weight of the polymer coated on the drug crystals is divided by the total weight of the drug, including any salts, waters of hydration, or solvates present in the solubility-improved drug form.

Excipients and Dosage Forms

Although the key ingredients present in the dosage forms of the present invention are simply the drug and polymer, the dosage form may include one or more excipients. Excipients may be utilized to formulate the drug and polymer into tablets, capsules, suspensions, powders for suspension, creams, transdermal patches, depots, and the like.

One very useful class of excipients is surfactants. Suitable surfactants include fatty acid and alkyl sulfonates; commercial surfactants such as benzethanium chloride (HYAMINE® 1622, available from Lonza, Inc., Fairlawn, N.J.); DOCUSATE SODIUM (available from Mallinckrodt Spec. Chem., St. Louis, Mo.); polyoxyethylene sorbitan fatty acid esters (TWEEN®, available from ICI Americas Inc., Wilmington, Del.); LIPOSORB® P-20 (available from Lipochem Inc., Patterson N.J.); CAPMUL® POE-0 (available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug. These surfactants may comprise up to 5 wt % of the composition.

The addition of pH modifiers such as acids, bases, or buffers may also be beneficial, retarding or enhancing the rate of dissolution of the composition, or, alternatively, helping to improve the chemical stability of the composition.

Other conventional formulation excipients may be employed in the dosage forms of this invention, including those excipients well-known in the art (e.g., as described in *Remington: The Science and Practice of Pharmacy* (20$^{th}$ ed. 2000). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the drug/polymer composition has been formed, in order to formulate the composition into tablets, capsules, suspensions, powders for suspension, creams, transdermal patches, and the like.

Examples of fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of drug complexing agents or solubilizers include the polyethylene glycols, caffeine, xanthene, gentisic acid and cyclodextrins.

Examples of disintegrants include sodium starch glycolate, sodium carboxymethyl cellulose, calcium carboxymethyl cellulose, croscarmellose sodium, crospovidone (polyvinylpolypyrrolidone), methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of Glidants Include Silicon Dioxide, Talc and Cornstarch.

Compositions of low-solubility drug and polymer of this invention may be used in a wide variety of dosage forms for administration of drugs. Exemplary dosage forms are powders or granules that may be taken orally either dry or reconstituted by addition of water to form a paste, slurry, suspension or solution; tablets; capsules; multiparticulates; and pills. Various additives may be mixed, ground, or granulated with the compositions of this invention to form a material suitable for the above dosage forms.

In some cases, the overall dosage form or particles, granules or beads that make up the dosage form may have superior performance if coated with an enteric polymer to prevent or retard dissolution until the dosage form leaves the stomach. Exemplary enteric coating materials include HPMCAS, HPMCP, CAP, CAT, carboxymethylethyl cellulose, carboxylic acid-functionalized polymethacrylates, and carboxylic acid-functionalized polyacrylates.

Compositions of low-solubility drug and polymer of this invention may be administered in a controlled release dosage form. In one such dosage form, the composition of the drug and polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the particles of low-solubility drug that are at least partially coated with a precipitation-inhibiting polymer. The aqueous-swollen matrix gradually erodes, swells, disintegrates or dissolves in the environment of use, thereby controlling the release of the drug mixture to the environment of use.

Alternatively, the compositions of low-solubility drug and polymer of the present invention may be administered by or incorporated into a non-erodible matrix device.

Alternatively, the drug and polymer may be delivered using a coated osmotic controlled release dosage form. This dosage form has two components: (a) the core which contains an osmotic agent and the coated drug particles; and (b) an outer coating surrounding the core, the outer coating controlling the influx of water to the core from an aqueous environment of use so as to cause drug release by extrusion of some or all of the core to the environment of use. The osmotic agent contained in the core of this device may be an aqueous-swellable hydrophilic polymer, hydrogel, osmogen, or osmagent. The outer coating surrounding the core is preferably polymeric, aqueous-permeable, and has at least one delivery port.

Alternatively, the drug and polymer may be delivered via a coated hydrogel controlled release dosage form having three components: (a) a drug-containing composition containing the coated drug particles, (b) a water-swellable composition wherein the water-swellable composition is in a separate region within a core formed by the drug-containing composition and the water-swellable composition, and (c) an outer coating around the core that is water-permeable, and has at least one delivery port therethrough. In use, the core imbibes water through the outer coating, swelling the water-swellable composition and increasing the pressure within the core, and fluidizing the drug-containing composition. Because the outer coating surrounding the core remains intact, the drug-containing composition is extruded out of the delivery port into an environment of use.

In one embodiment, the dosage form provides controlled release of at least a portion of the drug contained in the dosage form over a sustained length of time. Such an embodiment may have utility where it is desired to release at least a portion of the drug in the small intestine, the colon, or both. In this embodiment, the drug may be coated with an enteric, precipitation-inhibiting polymer. Preferred enteric precipitation-inhibiting polymers include HPMCAS, CAP, CAT, HPMCP, and CMEC. The drug particles may be fully encapsulated with the precipitation-inhibiting polymer to prevent early dissolution of the drug in a gastric environment. The precipitation-inhibiting polymer may be water impermeable at low pH to prevent the drug from dissolving and leaching out of the dosage form in the gastric environment. This embodiment has particular utility for providing controlled release of low-solubility, basic drugs to the small intestine or colon.

In addition to the above additives or excipients, use of any conventional materials and procedures for preparation of suitable dosage forms using the compositions of this invention known by those skilled in the art are potentially useful.

Other features and embodiments of the invention will become apparent from the following examples that are given for illustration of the invention rather than for limiting its intended scope.

EXAMPLES

Coated Crystals 1 (CC-1)

In this example, ziprasidone hydrochloride monohydrate crystals were coated with the precipitation-inhibiting polymer hydroxypropyl methyl cellulose acetate succinate (HPMCAS) to form particles of a solubility-improved drug form at least partially coated with a precipitation-inhibiting polymer.

A microcentrifuge dissolution test was performed to verify that ziprasidone hydrochloride monohydrate is a solubility-improved form of ziprasidone. For this test, a sufficient amount of ziprasidone hydrochloride monohydrate was added to a microcentrifuge test tube so that the concentration of ziprasidone would have been 200 µgA/mL, if all of the ziprasidone had dissolved. The tests were run in duplicate. The tubes were placed in a 37° C. temperature-controlled chamber, and 1.8 mL MFD solution at pH 6.5 and 290 mOsm/kg was added to each respective tube. The samples were quickly mixed using a vortex mixer for about 60 seconds. The samples were centrifuged at 13,000 G at 37° C. for 1 minute prior to collecting a sample. The resulting supernatant solution was then sampled and diluted 1:5 (by volume) with methanol. Samples were analyzed by high-performance liquid chromatography (HPLC) at a UV absorbance of 315 nm using a Zorbax RxC8 Reliance column and a mobile phase consisting of 55% (50 mM potassium dihydrogen phosphate, pH 6.5)/45% acetonitrile. Drug concentration was calculated by comparing UV absorbance of samples to the absorbance of drug standards. The contents of each tube were mixed on the vortex mixer and allowed to stand undisturbed at 37° C. until the next sample was taken. Samples were collected at 4, 10, 20, 40, 90, and 1200 minutes following administration to the MFD solution. The results are shown in Table 1.

A similar test was performed with the crystalline ziprasidone free base as a control, and a sufficient amount of material was added so that the concentration of compound would have been 200 μgA/mL, if all of the ziprasidone had dissolved.

TABLE 1

| Salt Form | Time (min) | Dissolved Ziprasidone Concentration (μgA/mL) | AUC (min-μgA/mL) |
|---|---|---|---|
| Ziprasidone Free Base | 0 | 0 | 0 |
| | 4 | 1 | 3 |
| | 10 | 1 | 11 |
| | 20 | 1 | 23 |
| | 40 | 2 | 51 |
| | 90 | 1 | 120 |
| | 1200 | 2 | 2000 |
| Ziprasidone hydrochloride monohydrate | 0 | 0 | 0 |
| | 4 | 14 | 30 |
| | 10 | 15 | 110 |
| | 20 | 20 | 280 |
| | 40 | 22 | 700 |
| | 90 | 18 | 1,700 |
| | 1200 | 9 | 16,400 |

The concentrations of ziprasidone obtained in these tests were used to determine the maximum dissolved concentration of ziprasidone ("$MDC_{90}$") and the area under the concentration-versus-time curve ("$AUC_{90}$") during the initial ninety minutes. The results are shown in Table 2.

TABLE 2

| Salt Form | $MDC_{90}$ (mgA/mL) | $AUC_{90}$ (min*mgA/mL) |
|---|---|---|
| Ziprasidone Free Base | 2 | 120 |
| Ziprasidone hydrochloride monohydrate | 22 | 1,700 |

These results show that ziprasidone hydrochloride monohydrate provided an $MDC_{90}$ that was 11-fold that provided by the free base, and an $AUC_{90}$ that was 14-fold that provided by the free base. Thus, the hydrochloride salt form is a solubility-improved form of ziprasidone.

A spray drying process was used to form particles of ziprasidone hydrochloride monohydrate at least partially coated with HPMCAS, as follows. The CC-1 formulation contained 39.7 wt % jet-milled ziprasidone hydrochloride monohydrate coated with the precipitation-inhibiting polymer HPMCAS-HG (AQOAT-HG, manufactured by Shin Etsu, Tokyo, Japan). Thus, the weight ratio of polymer to drug was 1.52.

Jet-milled ziprasidone was prepared as follows. The ziprasidone dry powder was slowly poured into a Glen Mills Laboratory Jet Mill, with two nitrogen lines set at about 100 psi. Milled material was collected in a receiving jar.

A spray suspension was then formed containing 3.97 wt % jet-milled ziprasidone hydrochloride monohydrate, 6.03 wt % HPMCAS-HG, and 90 wt % acetone. The acetone and HPMCAS-HG were combined in a container and mixed with a top-mounted mixer, dissolving the HPMCAS in the acetone. Jet-milled ziprasidone was added to the polymer solution and mixing continued with a top-mounted mixer, forming a suspension of the ziprasidone in the polymer/acetone solution. Next, a re-circulation pump (Yamada air actuated diaphragm pump model NDP-5FST) was used to move the suspension to a high-shear in-line mixer (Bematek model LZ-150-6-PB multi-shear in-line mixer) equipped with a series of rotor/stator shear heads to break up any remaining drug crystal agglomerations. The high shear mixer was operated with a setting of 3500±500 rpm, for 45-60 minutes per 20 kg solution. The re-circulation pump pressure was 35±10 psig.

The suspension was then pumped using a high-pressure pump to a spray dryer (a Niro type XP Portable Spray-Dryer with a Liquid-Feed Process Vessel ("PSD-1")), equipped with a pressure nozzle (Spraying Systems Pressure Nozzle and Body) (SK 74-20). The PSD-1 was equipped with a 5-foot 9-inch chamber extension. The chamber extension was added to the spray dryer to increase the vertical length of the dryer. The added length increased the residence time within the dryer, which allowed the product to dry before reaching the angled section of the spray dryer. The spray dryer was also equipped with a 316 SS circular diffuser plate with 1/16-inch drilled holes, having a 1% open area. This small open area directed the flow of the drying gas to minimize product recirculation within the spray dryer. The nozzle sat flush with the diffuser plate during operation. The suspension was delivered to the nozzle at about 285 g/min at a pressure of about 350 psig. The pump was followed by a pulsation dampener to minimize pulsation at the nozzle. Drying gas (e.g., nitrogen) was delivered through the diffuser plate at a flow rate of 1550 g/min, and an inlet temperature of 140° C. The evaporated solvent and wet drying gas exited the spray drier at a temperature of 40° C. The coated crystals formed by this process were collected in a cyclone, then post-dried using a Gruenberg single-pass convection tray dryer operating at 40° C. for 4 hours. The properties of the coated crystals after secondary drying were as follows:

TABLE 3

| Parameter | Value |
|---|---|
| Morphology | Spherical and wrinkled particles |
| Mean particle diameter (μm) | 44 |
| *$Dv_{10}$, $Dv_{50}$, $Dv_{90}$ (μm) | 13, 40, 81 |
| Span ($D_{90}$-$D_{10}$)/$D_{50}$ | 1.7 |
| Bulk specific volume (cc/g) | 4.14 |
| Tapped specific volume (cc/g) | 2.65 |
| Hausner ratio | 1.56 |

*10 vol % of the particles have a diameter that is smaller than $D_{10}$; 50 vol % of the particles have a diameter that is smaller than $D_{50}$, and 90 vol % of the particles have a diameter that is smaller than $D_{90}$.

In Vitro Dissolution Test

This describes an in vitro membrane permeation test, used to demonstrate that the coated crystals CC-1 provided concentration-enhancement of ziprasidone in vitro. An Accurel® PP 1E microporous polypropylene membrane was obtained from Membrana GmbH (Wuppertal, Germany). The membrane was washed in isopropyl alcohol and rinsed in methanol in a sonicating bath for 1 minute at ambient temperature, and then allowed to air dry at ambient temperature. The feed side of the membrane was then plasma-treated to render it hydrophilic by placing a sample of the membrane in a plasma chamber. The atmosphere of the plasma chamber was saturated with water vapor at a pressure of 550 mtorr. A plasma was then generated using radio frequency (RF) power inductively coupled into the chamber via annular electrodes at a power setting of 50 watts for 45 seconds. The contact angle of a drop of water placed on the surface of the plasma-treated membrane was less than about 40°. The contact angle of a drop of water placed on the permeate side of the same membrane was greater than about 110°.

A permeate reservoir was formed by gluing a sample of the plasma-treated membrane to a glass tube having an inside diameter of about 1 inch (2.54 cm) using an epoxy-based glue (LOCTITE® E-30CL HYSOL® from Henkel Loctite Corp, Rocky Hill, Conn.). The feed-side of the membrane was oriented so that it was on the outside of the permeate reservoir, while the permeate-side of the membrane was oriented so that it was on the inside of the reservoir. The effective membrane area of the membrane on the permeate reservoir was about 4.9 cm². The permeate reservoir was placed into a glass feed reservoir. The feed reservoir was equipped with a magnetic stir bar and the reservoir was placed on a stir plate and the stir rate was set to 100 rpm during the test. The apparatus was placed into a chamber maintained at 37° C. for the duration of the test. Further details of the test apparatus and protocols are presented in co-pending U.S. Patent Application Ser. No. 60/557,897, entitled "Method and Device for Evaluation of Pharmaceutical Compositions," filed Mar. 30, 2004, incorporated herein by reference.

To form the feed solution, a 1.429 mg (0.5 mgA) sample of CC-1 was weighed into a feed reservoir. (As used herein, "mgA" is milligrams of active drug, reported as the free base, non-salt form, non-hydrate drug molecule.) To this was added 5 mL of the MFD solution previously described, consisting of PBS solution containing 7.3 mM sodium taurocholic acid and 1.4 mM of 1-palmitoyl-2-oleyl-sn-glycero-3-phosphocholine (0.5% NaTC/POPC). The concentration of ziprasidone in the feed solution would have been 100 mg/mL, if all of the drug had dissolved. The feed solution was mixed using a vortex mixer for 1 minute. Before the membrane contacted the feed solution, 5 mL of 60 wt % decanol in decane was placed into the permeate reservoir. Time zero in the test was when the membrane was placed in contact with the feed solution. A 50 mL aliquot of the permeate solution was collected at the times indicated. Samples were then diluted in 250 mL IPA and analyzed using HPLC. The results are shown in Table 4.

Control 1A

Control 1A consisted of crystalline jet-milled ziprasidone hydrochloride monohydrate (Control 1 A) alone, in MFD solution, and a sufficient amount of material was added so that the concentration of drug would have been 100 μgA/mL, if all of the drug had dissolved.

Control 1B

Control 1B consisted of crystalline ziprasidone free-base alone, in MFD solution, and a sufficient amount of material was added so that the concentration of drug would have been 100 μgA/mL, if all of the drug had dissolved

TABLE 4

| Example | Time (min) | Ziprasidone Concentration in Permeate (μgA/mL) |
|---|---|---|
| CC-1 | 0 | 0.5 |
| | 20 | 4.5 |
| | 40 | 10.0 |

TABLE 4-continued

| Example | Time (min) | Ziprasidone Concentration in Permeate (μgA/mL) |
|---|---|---|
| | 60 | 15.5 |
| | 90 | 23.6 |
| | 120 | 31.9 |
| | 180 | 45.3 |
| | 240 | 56.2 |
| | 360 | 63.7 |
| Control 1A | 0 | 0.5 |
| Crystalline jet-milled ziprasidone hydrochloride monohydrate | 20 | 3.8 |
| | 40 | 6.0 |
| | 60 | 8.4 |
| | 90 | 12.4 |
| | 120 | 15.3 |
| | 180 | 20.6 |
| | 240 | 25.2 |
| | 360 | 30.6 |
| Control 1B | 0 | 0.0 |
| Crystalline ziprasidone free-base | 20 | 0.0 |
| | 40 | 3.3 |
| | 60 | 3.4 |
| | 90 | 5.4 |
| | 120 | 6.8 |
| | 180 | 9.2 |
| | 245 | 11.5 |
| | 360 | 14.7 |

The maximum flux of drug across the membrane (in units of μgA/cm²-min) was determined by performing a least-squares fit to the data in Table 4 from 0 to 60 minutes to obtain the slope (CC-1: 0.26 μgA/mL-min; Control 1A: 0.13 μgA/mL-min; Control 1B: 0.07 μgA/mL-min), multiplying the slope by the permeate volume (5 mL), and dividing by the membrane area (4.9 cm²). The results of this analysis are summarized in Table 5 and show that the maximum flux of ziprasidone through the membrane provided by the formulation of CC-1 was 2.0-fold that provided by Control 1A, and 3.7-fold that provided by Control 1B.

TABLE 5

| Sample | Formulation | Maximum Flux of Ziprasidone (μgA/cm²-min) |
|---|---|---|
| CC-1 | 39.7 wt % jet-milled ziprasidone hydrochloride monohydrate crystals coated with HPMCAS-HG | 0.26 |
| Control 1A | Crystalline jet-milled ziprasidone hydrochloride monohydrate | 0.13 |
| Control 1B | Crystalline ziprasidone free base | 0.07 |

Coated Crystals 2 (CC-2)

Crystals of ziprasidone hydrochloride monohydrate were coated with the "HF" grade of HPMCAS (AQOAT-HF, Shin Etsu) using the procedures outlined for CC-1, except that the ziprasidone hydrochloride monohydrate was not jet milled prior to coating. The coated crystals contained 39.7 wt % ziprasidone hydrochloride monohydrate. The properties of CC-2 are given in Table 6.

TABLE 6

| Parameter | Value |
| --- | --- |
| Morphology | Irregular spheres with evidence of crystalline particles |
| Mean particle diameter (μm) | 42 |
| *$Dv_{10}$, $Dv_{50}$, $Dv_{90}$ (μm) | 13, 38, 76 |
| Span $(D_{90}-D_{10})/D_{50}$ | 1.6 |
| Bulk specific volume (cc/g) | 3.3 |
| Tapped specific volume (cc/g) | 2.2 |
| Hausner ratio | 1.5 |

An in vitro membrane permeation test was performed using the procedures outline for CC-1 to demonstrate that the coated crystals CC-2 provided concentration-enhancement of ziprasidone in vitro. Table 7 shows the concentration of drug in the permeate solution versus time.

Control 2

Control 2 consisted of crystalline ziprasidone hydrochloride monohydrate (Control 2) alone, in MFD solution, and a sufficient amount of material was added so that the concentration of drug would have been 100 μgA/mL, if all of the drug had dissolved.

TABLE 7

| Formulation | Time (min) | Concentration (μgA/mL) |
| --- | --- | --- |
| CC-2 | 0 | 0.0 |
|  | 20 | 3.4 |
|  | 40 | 13.2 |
|  | 60 | 17.5 |
|  | 90 | 25.2 |
|  | 120 | 33.3 |
|  | 180 | 47.9 |
|  | 240 | 48.4 |
|  | 360 | 52.4 |
| Control 2 | 0 | 0.5 |
|  | 20 | 5.2 |
|  | 40 | 8.1 |
|  | 60 | 10.0 |
|  | 90 | 11.4 |
|  | 120 | 12.9 |
|  | 180 | 18.1 |
|  | 240 | 20.9 |
|  | 360 | 22.6 |

The maximum flux of drug across the membrane was determined by performing a least-squares fit to the data in Table 7 from 0 to 60 minutes to obtain the slope (CC-2: 0.32 μgA/mL-min; Control 2: 0.16 μgA/mL-min), multiplying the slope by the permeate volume (5 mL), and dividing by the membrane area (4.9 cm$^2$). The results of this analysis are summarized in Table 8. These data show that the maximum flux of ziprasidone through the membrane provided by the formulation of CC-2 was 2.0-fold that provided by Control 2.

TABLE 8

| Sample | Formulation | Maximum Flux of Ziprasidone (μgA/cm$^2$-min) |
| --- | --- | --- |
| CC-2 | 39.7 wt % ziprasidone hydrochloride monohydrate crystals coated with HPMCAS-HG | 0.32 |
| Control 2 | Crystalline ziprasidone hydrochloride monohydrate | 0.16 |

Coated Crystals 3 (CC-3)

Crystals of ziprasidone tosylate, a solubility-improved form of ziprasidone, were coated with the "HF" grade of HPMCAS (AQOAT-HF, Shin Etsu) using the procedures outlined for CC-1, with the following exceptions. The spray suspension was formed by first dissolving 12.07 μm HPMCAS-HF into 225 μm acetone and then suspending 12.94 μm of ziprasidone tosylate in the resulting solution. The coated crystals contained 52 wt % ziprasidone tosylate, corresponding to a weight ratio of HPMCAS to ziprasidone tosylate of 0.92.

An in vitro membrane permeation test was performed using the procedures outline for CC-1 to demonstrate that the coated crystals CC-3 provided concentration-enhancement of ziprasidone in vitro. Table 9 shows the concentration of drug in the permeate solution versus time.

Control 3

Control 3 consisted of crystalline ziprasidone tosylate (Control 3) alone, in MFD solution, and a sufficient amount of material was added so that the concentration of drug would have been 100 μgA/mL, if all of the drug had dissolved.

TABLE 9

| Formulation | Time (min) | Concentration (μgA/mL) |
| --- | --- | --- |
| CC-3 | 0 | 0.0 |
|  | 20 | 14.4 |
|  | 40 | 23.9 |
|  | 60 | 28.3 |
|  | 90 | 31.7 |
|  | 120 | 34.9 |
|  | 180 | 38.4 |
|  | 240 | 42.8 |
|  | 300 | 46.5 |
|  | 360 | 51.3 |
| Control 3 | 0 | 0.0 |
|  | 20 | 0.7 |
|  | 40 | 1.6 |
|  | 60 | 2.5 |
|  | 90 | 3.6 |
|  | 120 | 4.6 |
|  | 180 | 7.1 |
|  | 240 | 10.1 |
|  | 300 | 12.6 |
|  | 360 | 14.7 |

The maximum flux of drug across the membrane was determined by performing a least-squares fit to the data in Table 9 from 0 to 60 minutes to obtain the slope (CC-3: 0.47 μgA/mL-min; Control 3: 0.04 μgA/mL-min), multiplying the slope by the permeate volume (5 mL), and dividing by the membrane area (4.9 cm$^2$). The results of this analysis are summarized in Table 10 and show that the maximum flux of ziprasidone through the membrane provided by the formulation of CC-3 was 12-fold that provided by Control 3.

TABLE 10

| Sample | Formulation | Maximum Flux of Ziprasidone (μg/cm$^2$-min) |
| --- | --- | --- |
| CC-3 | 52 wt % ziprasidone tosylate crystals coated with HPMCAS-HF | 0.48 |
| Control 3 | Crystalline ziprasidone tosylate | 0.04 |

Coated Crystals 4 (CC-4)

In this example, sildenafil citrate, a solubility-improved form of sildenafil, was coated with the precipitation-inhibiting polymer HPMCAS to form particles of a solubility-improved drug form at least partially coated with a precipitation-inhibiting polymer.

A spray drying process was used to form particles of sildenafil citrate coated with HPMCAS, as follows. The CC-4 formulation contained 75 wt % sildenafil citrate coated with the precipitation-inhibiting polymer HPMCAS-HG (AQOAT-HG, manufactured by Shin Etsu). First, a spray suspension was formed containing 50 g sildenafil citrate, 16.65 g HPMCAS-HG, and 266.6 g acetone. The acetone and HPMCAS-HG were combined in a container and mixed with a top-mounted mixer, dissolving the HPMCAS in the acetone. Sildenafil citrate was added to the polymer solution to form a suspension of the drug crystals, and mixing continued with a top-mounted mixer as described for CC-1. A re-circulation pump was used to move the suspension to a high-shear in line mixer. The high shear mixer was operated with a setting of 5000 rpm, for 7 minutes.

The suspension was then pumped using a high-pressure pump to the spray drier described in CC-1. The PSD-1 was equipped with a 9-inch chamber extension. The suspension was delivered to a Spraying Systems pressure nozzle SK 76-16 at about 160 g/min at a pressure of about 200 psi. Drying gas (e.g., nitrogen) was delivered through the diffuser plate, with an inlet temperature of 105° C. The evaporated solvent and wet drying gas exited the spray drier at a temperature of 48° C. The coated crystals formed by this process were collected in a cyclone, then post-dried using a Gruenberg single-pass convection tray dryer operating at 30° C. for 20 hours. The resulting coated crystals of sildenafil had a ratio of HPMCAS to drug of 0.33.

In Vitro Dissolution Test

The coated drug crystals of CC-4, and crystalline drug alone (Control 4), were evaluated using a nuclear magnetic resonance (NMR) test to show that CC-4 provided concentration-enhancement. In this test, 3.276 mg of the coated crystals CC-4, or 2.542 mg of Control 4 (sildenafil citrate alone), was added to microcentrifuge tubes in duplicate. The tubes were placed in a 37° C. temperature-controlled chamber, and 1.8 mL of deuterated PBS solution at pH 6.5 and 290 mOsm/kg, with 3-(trimethylsilyl)propionic-2,2,3,3-$d_4$ acid, sodium salt ("TSP"; a deuterated NMR reference standard), was added. The samples were quickly mixed using a vortex mixer for 60 seconds. The suspension was then immediately transferred to an 8 mm glass NMR tube and acquisition was started as soon as possible.

Proton spectra of the sample were recorded at 300.070 MHz on a Varian Gemini 2000, 300 MHz NMR equipped with a Nalorac 8 mm indirect detection probe. The sample temperature was maintained at 37° C. in the probe and the spectra acquired using a 90° pulse width and 14 second pulse delay (delay>5*$t_{1\ drug\ or\ standard}$). Ten consecutive free induction decay signals (FIDs) were collected to determine the concentration, with each FID consisting of 120 pulses (30 minutes per FID). The listed time for each concentration result (i.e., FID) was calculated from the time the PBS solution was added to the solid sample until half of the time the FID had been acquired. For example, when the second FID was recorded for a sample that was started 5 minutes after the addition of PBS, the time listed for the NMR result was 50 minutes (5 min+30 min [time for the first FID result]+½ of 30 min [time of second FID result]). Aromatic drug resonances were integrated relative to the internal standard peak and the drug concentration determined.

The results of this test are summarized in Table 11, which shows the concentration of sildenafil in solution for CC-4 and Control 4. The coated crystals CC-4 provided an enhanced dissolved drug concentration over that of the control.

TABLE 11

| Sample | Time (min) | Sildenafil Concentration (µgA/mL) |
|---|---|---|
| CC-4 | 20 | 185 |
| | 50 | 163 |
| | 80 | 153 |
| | 110 | 150 |
| | 140 | 143 |
| | 170 | 145 |
| | 200 | 133 |
| | 230 | 127 |
| | 260 | 134 |
| | 290 | 127 |
| Control 4 crystalline sildenafil citrate | 30 | 27 |
| | 60 | 24 |
| | 90 | 25 |
| | 120 | 24 |
| | 150 | 21 |
| | 180 | 21 |
| | 210 | 24 |
| | 240 | 27 |
| | 270 | 25 |
| | 300 | 28 |
| | 330 | 22 |
| | 360 | 21 |
| | 390 | 33 |

Dosage Form DF-1

Dosage Form DF-1 was prepared using coated crystals CC-2, consisting of 39.7 wt % ziprasidone hydrochloride monohydrate coated with HPMCAS-HF. Dosage Form DF-1 was prepared using the following procedure.

Preparation of the Drug-Containing Composition

To form the drug-containing composition, the following materials were blended: 24.99 wt % CC-2, 74.01 wt % polyethylene oxide (PEO WSR N80), and 1.00 wt % magnesium stearate. The drug-containing composition ingredients were first combined with 0.25 wt % magnesium stearate and blended for 15 minutes in a 16 quart V-blender. Next, the ingredients were roller-compacted using a Vector TF mini roller-compactor, then milled using a Fitzpatrick M5A mill. Finally, the drug-containing composition was blended an additional 10 minutes, the remaining magnesium stearate (0.75 wt %) was added, and the ingredients were blended again for 5 minutes.

Preparation of the Water-Swellable Composition

To form the water-swellable composition, the following materials were blended: 65.0 wt % polyethylene oxide (PEO WSR coagulant), 34.3 wt % sodium chloride, 0.5 wt % magnesium stearate, and 0.2 wt % Blue Lake #2. All ingredients except magnesium stearate were combined and blended for 15 minutes, then milled using a Fitzpatrick M5A mill. The ingredients were blended an additional 10 minutes, the magnesium stearate was added, and the mixture was blended again for 5 minutes.

Preparation of Tablet Cores

Bilayer tablet cores were manufactured using an Elizabeth-Hata trilayer press combining 453 mg of the drug-containing composition and 227 mg of the water-swellable composition using 7/16-inch standard round concave (SRC) plain-faced tooling. The tablet cores were compressed to a hardness of about 8 kiloponds (kp). The resulting bi-layer tablet core had a total weight of 680 mg and contained a total of 40 mg active ziprasidone.

Application of the Coating

Coatings for the tablet cores were applied in a Vector LDCS-20 pan coater. The coating solution for DF-1 contained cellulose acetate (CA 398-10 from Eastman Fine Chemical, Kingsport, Tenn.), polyethylene glycol (PEG 3350, Union Carbide), water, and acetone in a weight ratio of 6.8/1.2/4/88 (wt %). The flow rate of the inlet heated drying gas of the pan coater was set at 40 ft$^3$/min with the outlet temperature set at 25° C. Nitrogen at 20 psi was used to atomize the coating solution from the spray nozzle, with a nozzle-to-bed distance of 2 inches. The pan rotation was set to 20 rpm. The so-coated tablets were dried 16 hr at 40° C. in a tray-drier. The final dry coating weight amounted to about 8.1 wt % of the tablet core. One 900 μm diameter hole was laser-drilled in the coating on the drug-containing composition side of each of the tablets of DF-1 to provide one delivery port per tablet. Each tablet of DF-1 contained 40 mgA of ziprasidone.

Dosage Form DF-2

Dosage Form DF-2 was prepared using the same procedure outlined for DF-1 except that the coating amounted to 10 wt % of the core weight. Each tablet of DF-2 contained 40 mgA of ziprasidone.

Dosage Form DF-3

Dosage Form DF-3 was prepared using the procedures outlined for DF-1 except that the drug-containing composition used coated crystals CC-1. The coating solution contained CA 398-10, PEG 3350, water, and acetone in a weight ratio of 4.25/0.75/2.5/92.5 (wt %), and amounted to 7.8 wt % of the core weight. Each tablet of DF-3 contained 40 mgA of ziprasidone.

Dosage Form DF-4

Dosage Form DF-4 was prepared using the same procedure outlined for DF-3 except that the coating amounted to 10.2 wt % of the core weight. Each tablet of DF-4 contained 40 mgA of ziprasidone.

Dosage Form DF-5

Dosage Form DF-5 consisted of a matrix sustained-release tablet made using coated crystals CC-2. The matrix tablets consisted of 42 wt % of the coated crystals CC-2, 42 wt % sorbitol, 15 wt % HPMC (K100LV), and 1 wt % magnesium stearate. The tablets were prepared by first blending the coated crystals, sorbitol, and HPMC in a twin-shell blender for 20 minutes, milling using a Fitzpatric M5A mill, and then blending in the twin-shell blender for an additional 20 minutes. The magnesium stearate was then added and the mixture blended again for 5 minutes. The tablets were manufactured using an F press using 555.5 mg of the mixture using 11-mm SRC plain-faced tooling. The tablet cores were compressed to a hardness of about 11 kp. The resulting sustained-release matrix tablet contained a total of 80 mg active ziprasidone.

Dosage Form DF-6

Dosage Form DF-6 consisted of a matrix sustained-release tablet made using coated crystals CC-2. The matrix tablets consisted of 30 wt % of the coated crystals CC-2, 29 wt % spray-dried lactose, 40 wt % PEO WSRN-10 (100,000 daltons), and 1 wt % magnesium stearate. The tablets were prepared by first blending the coated crystals, lactose, and PEO in a twin-shell blender for 20 minutes, milling using a Fitzpatric M5A mill, and then blending in the twin-shell blender for an additional 20 minutes. The magnesium stearate was then added and the mixture blended again for 5 minutes. The tablets were manufactured using an F press using 381 mg of the mixture using caplet-shaped tooling with dimensions 0.30 inches by 0.60 inches. The tablet cores were compressed to a hardness of about 13 kp. The resulting sustained-release matrix tablet contained a total of 40 mg active ziprasidone.

Dosage Form DF-7

Dosage Form DF-7 consisted of Dosage Form DF-6 that had been coated with an enteric coating. The coating solution consisted of 41.7 wt % Eudragit L30-D55 and 2.5 wt % triethylcitrate in 55.8 wt % water. Coatings were applied in an LDCS-20 pan coater. The coating weight was 10 wt % of the uncoated core weight. The resulting sustained-release matrix tablet contained at total of 40 mg active ziprasidone.

Dosage Form DF-8

A bilayer osmotic dosage form containing coated crystals of ziprasidone tosylate (CC-3) was prepared using the following procedures.

Preparation of the Drug-Containing Composition

To form the drug-containing composition, the following materials were blended: 25.0 wt % CC-3, 74.0 wt % PEO WSR N80, and 1.0 wt % magnesium stearate. The drug-containing composition ingredients were first combined without magnesium stearate, blended for 20 minutes in a Turbula mixer, passed through a 20 mesh sieve, and blended again for 20 minutes. One half of the magnesium stearate was then added to the blend and the mixture blended for an additional 4 minutes. Next, the ingredients were compressed to 4 kP using an F press with ½-inch standard round concave tooling, ground using a mortar and pestle, and passed through a 20 mesh sieve. Finally, the remaining magnesium stearate was added, and the ingredients were blended again for 4 minutes.

Preparation of the Water-Swellable Composition

To form the water-swellable composition, the following materials were blended: 65.0 wt % PEO WSR coagulant, 34.3 wt % sodium chloride, 0.5 wt % magnesium stearate, and 0.2 wt % Blue Lake #2. All ingredients except magnesium stearate were combined and blended for 20 minutes, passed through a 20 mesh sieve, and blended again for 20 minutes. The magnesium stearate was added, and the mixture was blended for 4 minutes.

Preparation of Tablet Cores

Bilayer tablet cores were manufactured using an F press combining 453 mg of the drug-containing composition and 227 mg of the water-swellable composition with 7/16-inch SRC tooling. The tablet cores were compressed to a hardness of about 11 kp. The resulting bi-layer tablet core had a total weight of 680 mg and contained a total of 40 mg active ziprasidone.

Application of the Coating

Coatings for the tablet cores were applied in a Vector LDCS-20 pan coater. The coating solution contained CA 398-10, PEG 3350, water, and acetone in a weight ratio of 4.25/0.75/2.5/92.5 (wt %). The flow rate of the inlet heated drying gas of the pan coater was set at 40 ft$^3$/m in with the outlet temperature set at 25° C. Nitrogen at 20 psi was used to atomize the coating solution from the spray nozzle, with a nozzle-to-bed distance of 2 inches. The pan rotation was set to 20 rpm. The so-coated tablets were dried 16 hr at 40° C. in a tray-drier. The final dry coating weight amounted to about 10.35 wt % of the tablet core. One 900 μm diameter hole was laser-drilled in the coating on the drug-containing composition side of each of the tablets to provide one delivery port per tablet.

Dosage Form DF-9

Dosage Form DF-9 consisted of a single-layer osmotic tablet that provided sustained release of ziprasidone. The dosage form contained coated crystals of ziprasidone hydrochloride monohydrate (CC-2). The tablet core consisted of 26.5 wt % of the coated crystals CC-2, 60.0 wt % sorbitol, 8.0 wt % hydroxy ethyl cellulose (Natrosol 250HX), 1.5 wt % sodium lauryl sulfate (SLS), 3.0 wt % hydroxypropyl cellulose (Klucel EXF), and 1.0 wt % magnesium stearate. To form the tablet core, all of the ingredients except for the magnesium stearate were blended in a twin-shell blender for 15 minutes. The blend was then passed through a Fitzmill M5A equipped with a 0.031-inch Conidur rasping screen at 200 rpm. The blend was then returned to the twin-shell blender and blended an additional 15 minutes. One half of the magnesium stearate was then added to the blend and the mixture blended for an additional 3 minutes. The dry blend was then roller compacted using a Vector Feund TF Mini roller compactor with "S" rolls, using a roll pressure of 390 to 400 psi, a roller speed of 3-4 rpm, and a screw speed of 4-6 rpm. The roller compacted ribbons were then milled using the Fitzmill M5A. The milled material was then returned to a twin-shell blender and blended for 10 minutes, at which time the remaining magnesium stearate was added and the mixture blended for an additional 3 minutes. The tablet cores were then formed using a Killian T100 tablet press using 0.2838-inch by 0.5678-inch modified oval tooling. A coating was applied to the tablet core using the procedures outlined for DF-1, except that the coating solution contained CA 398-10, PEG 3350, water, and acetone in a weight ratio of 4.5/1.5/5/89 (wt %), and amounted to 7.5 wt % of the core weight. Each tablet of DF-9 contained 40 mgA of ziprasidone.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A process for making a dosage form comprising precipitation-inhibiting polymer-coated drug particles, the process comprising:
   providing particles of a low-solubility drug in a solubility-improved form selected from the group consisting of (1) a crystalline highly soluble form of the drug, (2) a high-energy crystalline form of the drug, and (3) a hydrate or solvate crystalline form of the drug;
   forming a suspension comprising the particles of the low-solubility drug, a precipitation-inhibiting polymer, and a solvent, wherein the precipitation-inhibiting polymer is dissolved in the solvent and less than 5 wt % of the particles of the low-solubility drug are dissolved in the solvent;
   spray drying the suspension to form precipitation-inhibiting polymer coated drug particles comprising a spray-dried coating of the precipitation-inhibiting polymer in direct contact with the particles of the low-solubility drug; and
   forming the precipitation-inhibiting polymer coated drug particles into a dosage form.

2. The process of claim 1, further comprising:
   combining the precipitation-inhibiting polymer coated drug particles with an excipient; and
   forming the precipitation-inhibiting polymer coated drug particles and the excipient into the dosage form.

3. The process of claim 1, further comprising coating the dosage form with an enteric polymer.

4. The process of claim 1, further comprising coating the precipitation-inhibiting polymer coated drug particles with an enteric polymer before forming the dosage form.

5. The process of claim 1, wherein a weight ratio of the precipitation-inhibiting polymer to the particles of the low-solubility drug is at least 0.11.

6. The process of claim 1, wherein the particles of the low-solubility drug have a solubility of less than 0.5 wt % in the solvent.

7. The process of claim 1, wherein the low-solubility drug is ziprasidone or a pharmaceutically acceptable salt thereof.

* * * * *